US008372935B2

(12) United States Patent
Maliverney et al.

(10) Patent No.: US 8,372,935 B2
(45) Date of Patent: Feb. 12, 2013

(54) COMPOUNDS WITH A GUANIDINE STRUCTURE AND USE THEREOF FOR AS ORGANOPOLYSILOXANE POLYCONDENSATION CATALYSTS

(75) Inventors: Christian Maliverney, Saint Julien sur Bibost (FR); Laurent Saint-Jalmes, Vourles (FR)

(73) Assignee: Bluestar Silicones France SAS, Lyons (FR)

( * ) Notice: Subject to any disclaimer, the term of this patent is extended or adjusted under 35 U.S.C. 154(b) by 193 days.

(21) Appl. No.: 12/809,024

(22) PCT Filed: Dec. 18, 2008

(86) PCT No.: PCT/FR2008/001767
§ 371 (c)(1),
(2), (4) Date: Sep. 28, 2010

(87) PCT Pub. No.: WO2009/106717
PCT Pub. Date: Sep. 3, 2009

(65) Prior Publication Data
US 2011/0046299 A1   Feb. 24, 2011

(30) Foreign Application Priority Data

Dec. 20, 2007 (FR) ...................................... 07 08925

(51) Int. Cl.
*C08G 77/26* (2006.01)
(52) U.S. Cl. .......................................... 528/21; 556/413
(58) Field of Classification Search .................... 528/21; 556/413
See application file for complete search history.

(56) References Cited

U.S. PATENT DOCUMENTS
4,248,993 A    2/1981   Takago

OTHER PUBLICATIONS

Kim et al. "Preparation of guanidine bases immobilized on SBA-15 mesoporous material and their catalytic activity in knoevenagel condensation" Studies in Surface Science and Catalysis, vol. 146 (2003) 505-508.*
International Search Report for PCT/EP2008/001767, dated Sep. 9, 2009(5 pages).

* cited by examiner

*Primary Examiner* — Kuo-Liang Peng
(74) *Attorney, Agent, or Firm* — Baker Donelson Bearman Caldwell & Berkowitz PC

(57) ABSTRACT

The invention relates to novel compounds with a guanidine structure, and more particularly nontoxic compounds with a silylated guanidine structure.

17 Claims, No Drawings

COMPOUNDS WITH A GUANIDINE STRUCTURE AND USE THEREOF FOR AS ORGANOPOLYSILOXANE POLYCONDENSATION CATALYSTS

CROSS REFERENCE TO RELATED APPLICATIONS

This application is a §371 National Stage Application of PCT/FR2008/001767 filed Dec. 18, 2008, which claims priority to French Application 07 08925 filed Dec. 20, 2007.

BACKGROUND OF THE INVENTION

1. Field of the Invention

The invention relates to compounds with a silylated guanidine structure, and to the uses thereof as catalysts for the polycondensation reaction of organopolysiloxanes.

The present invention relates to an organopolysiloxane composition that can be vulcanized at room temperature into an elastomer that is crosslinked by polycondensation and that does not contain alkyltin-based catalysts which exhibit toxicity problems.

The invention also relates to novel polycondensation catalysts in silicone chemistry, and to the uses thereof as catalysts for the polycondensation reaction of organopolysiloxanes.

2. Description of Related Art

Elastomer formulations that crosslink via polycondensation generally involve a silicone oil, generally a polydimethylsiloxane, with hydroxyl end groups, optionally prefunctionalized by a silane so as to have alkoxy ends, a crosslinker, a polycondensation catalyst, conventionally a tin salt or an alkyl titanate, a reinforcing filler and other optional additives such as bulking fillers, adhesion promoters, colorants, biocidal agents, etc.

These room-temperature vulcanizing organopolysiloxane compositions are well known and are classified into 2 different groups: single-component (RTV-1) compositions and two-component (RTV-2) compositions.

During crosslinking, water (either provided by atmospheric moisture in the case of RTV-1 compositions, or introduced into one part of the composition in the case of RTV-2 compositions) enables the polycondensation reaction, which results in the formation of the elastomeric network.

Generally, single-component (RTV-1) compositions crosslink when they are exposed to moisture from the air, that is to say that they cannot crosslink in an enclosed medium. For example, the single-component silicone compositions used as sealants or cold-setting adhesives follow a mechanism of hydrolysis of reactive functional groups of the acetoxysilane, ketiminoxysilane, alkoxysilane, etc. type, followed by condensation reactions between the silanol groups formed and other residual reactive functional groups. The hydrolysis is generally carried out by virtue of water vapor which diffuses into the material from the surface exposed to the atmosphere. Generally, the kinetics of the polycondensation reactions is extremely slow; these reactions are therefore catalyzed by a suitable catalyst. As catalysts which are used, use is most often made of catalysts based on tin, titanium, an amine or compositions of these catalysts. Catalysts based on tin (cf. in particular FR-A-2 557 582) and on titanium (cf. in particular FR-A-2 786 497) are catalysts that are very effective.

As regards two-component compositions, they are sold and stored in the form of two components, a first component containing the base polymer materials and the second component containing the catalyst. The two components are mixed at the moment of use and the mixture crosslinks in the form of a relatively hard elastomer. These two-component compositions are well known and are described, in particular, in the book by Walter Noll "Chemistry and Technology of Silicones" 1968, 2nd Edition, on pages 395 to 398. These compositions essentially comprise 4 different ingredients:

an $\alpha,\omega$-dihydroxydiorganopolysiloxane reactive polymer, a crosslinking agent, generally a silicate or a polysilicate, a tin catalyst, and water.

Usually, the condensation catalyst is based on an organic tin compound. Indeed, many tin-based catalysts have already been proposed as crosslinking catalysts for these RTV-2 compositions. The most widely used compounds are alkyltin carboxylates such as tributyltin monooleate or dialkyltin dicarboxylates such as dibutyltin dilaurate, dibutyltin diacetate or dimethyltin dilaurate (see the book by Noll "Chemistry and Technology of silicones" page 337, Academic Press, 1968-$2^{nd}$ Edition or patents EP 147 323 or EP 235 049).

However, the alkyltin-based catalysts, although very effective, usually colorless, liquid and soluble in silicone oils, have the drawback of being toxic (CMR2 toxic for reproduction).

Titanium-based catalysts, also widely used in RTV-1 compositions, have however a major drawback: they have slower kinetics than tin-based catalysts. Furthermore, these catalysts cannot be used in RTV-2 compositions due to gelling problems.

Other catalysts are sometimes mentioned, such as catalysts based on zinc, zirconium or aluminum, but they have only experienced minor industrial development due to their mediocre effectiveness.

Thus, catalysts of the polycondensation reaction of silicone have been developed that have a guanidine, such as tetramethylguanidine, structure, described in U.S. Pat. No. 3,719,633.

Other catalysts having a silylated guanidine structure were then developed and are described for example in U.S. Pat. No. 4,180,462 and U.S. Pat. No. 4,248,993.

Moreover, compounds having a silylated guanidine structure, such as tetramethyl-3-trimethoxysilylpropylguanidine described in U.S. Pat. No. 4,248,992 are also known. Such a compound is used as an antibacterial agent.

Moreover, catalysts of the Knoevenagel reaction are also known (KIM K. S., SONG J. H., KIM J. H., SEO G., Studies in Surface Science and Catalysis, 2003, 146, 505) of formula:

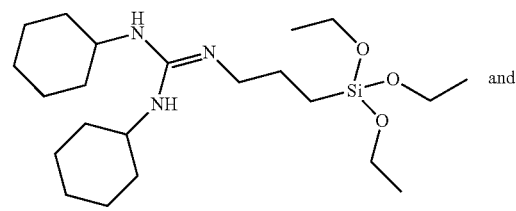

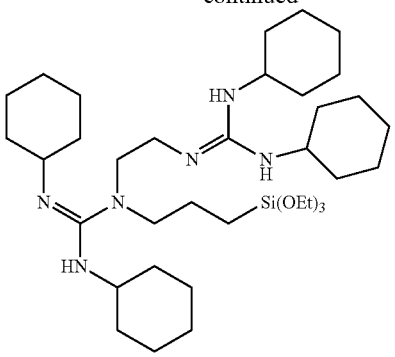

SUMMARY OF THE INVENTION

The main objective of the present invention is therefore to find a novel nontoxic catalyst that enables, in moisture from the air, both a surface crosslinking and a core crosslinking that is as complete as possible.

Another main objective of the present invention is to propose a catalyst system that can be used both in the crosslinking of single-component and two-component elastomer compositions.

Another main objective of the present invention is to propose a catalyst system that is nontoxic but that continues to simultaneously meet the constraints of storage, of processing and of crosslinking of the two types of single-component and two-component elastomer compositions.

These objectives, among others, are achieved by the present invention, which relates firstly to novel compounds that correspond to the general formula (I):

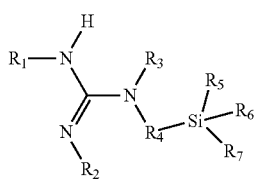

(I)

in which:

$R_1$ and $R_2$, which are identical or different, represent, independently of one another, a linear or branched monovalent alkyl group, a cycloalkyl group, a (cycloalkyl)alkyl group, the ring being substituted or unsubstituted and possibly comprising at least one heteroatom, an arylalkyl, fluoroalkyl, substituted or unsubstituted aryl or $R_{11}R_{12}R_{13}Si$ group, where $R_{11}$, $R_{12}$, and $R_{13}$ are linear or branched monovalent alkyl groups;

$R_3$ represents a hydrogen atom, a linear or branched monovalent alkyl group, a cycloalkyl group, an alkyl group substituted by a ring that is substituted or unsubstituted and that possibly comprises at least one heteroatom, an arylalkyl, fluoroalkyl, alkylamine, alkylguanidine or substituted or unsubstituted aryl group or an alkylalkoxysilane;

$R_4$ represents a linear or branched alkyl chain containing 1 to 50 atoms, preferably 1 to 20 atoms, some of them possibly being heteroatoms chosen from O, S and N;

$R_5$, $R_6$ and $R_7$, which are identical or different, represent, independently of one another, a linear or branched alkyl group, an aromatic group, an alkoxy group or a trialkylsilyloxy group of formula (I') below:

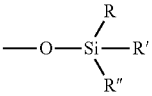

(I')

R, R' and R", which are identical or different, represent, independently of one another, a linear or branched $C_1$-$C_{12}$ alkyl group or an aromatic group; and on condition that:

if $R_3$ is a hydrogen atom, then $R_1$ and $R_2$ are not, either of them, a linear monovalent hydrocarbon-based group;

if $R_1$ and $R_2$ are each a cyclohexyl group, $R_4$ a linear propylene group and $R_5=R_6=R_7=OEt$, then $R_3$ is not a hydrogen atom; and if $R_1$ and $R_2$ are each a cyclohexyl group, $R_4$ a linear propylene group and $R_5=R_6=R_7=OEt$, then $R_3$ is not the group

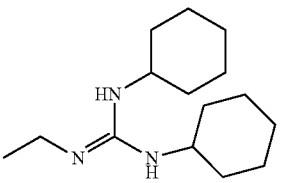 [SMILES: CCN=C(NC1CCCCC1)NC1CCCCC1]

DETAILED DESCRIPTION OF A PREFERRED EMBODIMENT

Although the tetramethylguanidine unit is known as a catalyst for crosslinking polyorganosiloxane oils, whether it is 1,1,3,3-tetramethylguanidine, used rather in the form of salts as a catalyst for functionalizing oils (U.S. Pat. No. 3,719,633 cited above), or in the alkylsilylated form, mainly 2-[3-(trialkoxysilyl)propyl]-1,1,3,3-tetramethylguanidines used as catalysts in single-component systems (U.S. Pat. No. 4,180,462 and U.S. Pat. No. 4,248,993 cited above), the compounds of the present invention are novel, particularly easy to obtain by the process claimed and faster and better performing as catalysts for the polycondensation of polyorganosiloxane oils, both in single-component systems and in two-component systems.

Moreover, the silylated, predominantly 2-(3-(trimethoxysilyl)propyl), 1,1,3,3-tetramethylguanidine systems of RN-CAS 69709-01-09 are pentasubstituted, whereas the silylated guanidines claimed in this patent are trisubstituted or tetrasubstituted.

Although a single trisubstituted silylated guanidine is known from the literature, 1,3-dicyclohexyl-2-(3-(triethoxysilyl)propyl)guanidine, of RN-CAS 680575-62-6, and also an analog having a double, trisubstituted and tetrasubstituted, guanidine structure, the 1,3-dicyclohexyl-2-(3-(triethoxysilyl)propyl)-2-(1,3-dicyclohexyl-2-ethylguanidinyl) guanidine of RN-CAS 680575-63-7, cited above, these are cited as catalysts of the Knoenenagel reaction, and therefore their use is very far from the use as catalysts for the polycondensation reaction of polyorganosiloxanes.

Preferably, $R_1$ and $R_2$ comprise from 1 to 8 carbon atoms.

A group of preferred compounds according to the invention corresponds to the compounds for which $R_1$ and $R_2$ are each an isopropyl or a cyclohexyl group.

$R_1$ and/or $R_2$ may also be a group of formula:

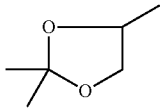

Another group of preferred compounds according to the invention corresponds to the compounds for which $R_3$ is a hydrogen atom, a methyl group, an ethyl group, a propyl group, a butyl group, a propyltrialkoxysilane group, a group:

—$(CH_2)_2NHC(NHiPr)(NiPr)$, or

—$(CH_2)_2NC(NHiPr)(NiPr)(CH_2)_2NHC(NHiPr)(NiPr)$.

Another group of preferred compounds according to the invention corresponds to the compounds for which $R_5$, $R_6$ and $R_7$, which are identical or different, represent, independently of one another, a linear $C_1$-$C_4$ alkyl group, preferably methyl, ethyl, or phenyl, an $OR_8$ group where $R_8$ is a linear or branched $C_1$-$C_8$ alkyl group, preferably a methyl, ethyl, propyl, isopropyl, butyl or trimethylsilyl group.

The compounds according to the invention are chosen from the compounds (1) to (55) below:

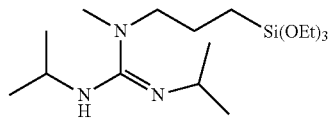

(1)

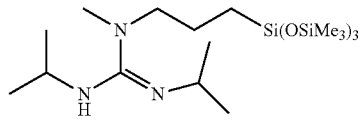

(2)

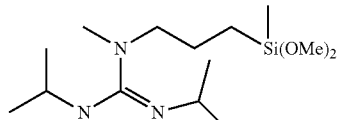

(3)

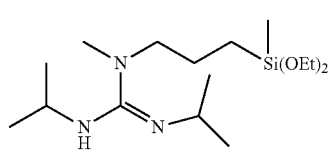

(4)

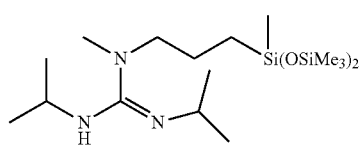

(5)

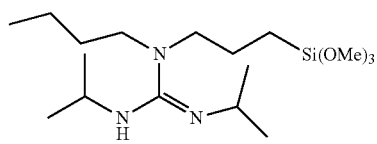

(6)

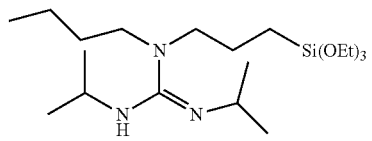

(7)

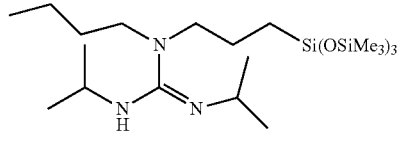

(8)

(9)

(10)

(11)

(12)

(13)

(14)

(15)

(16)

(17)

(18)

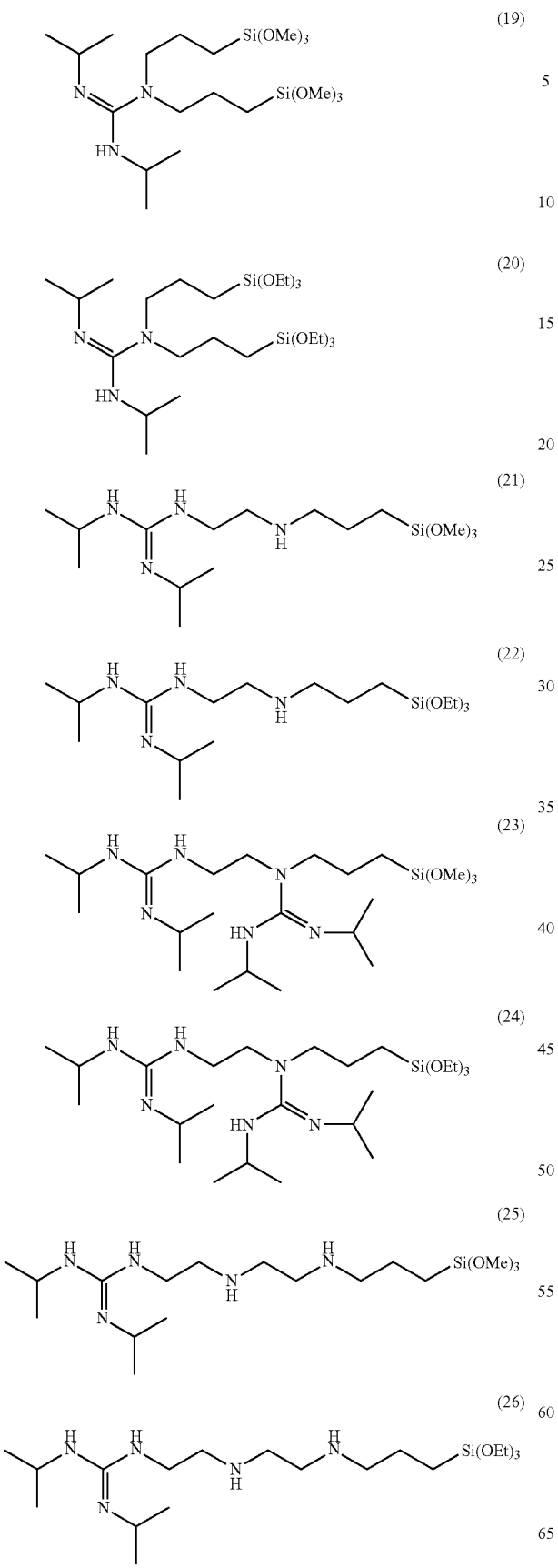
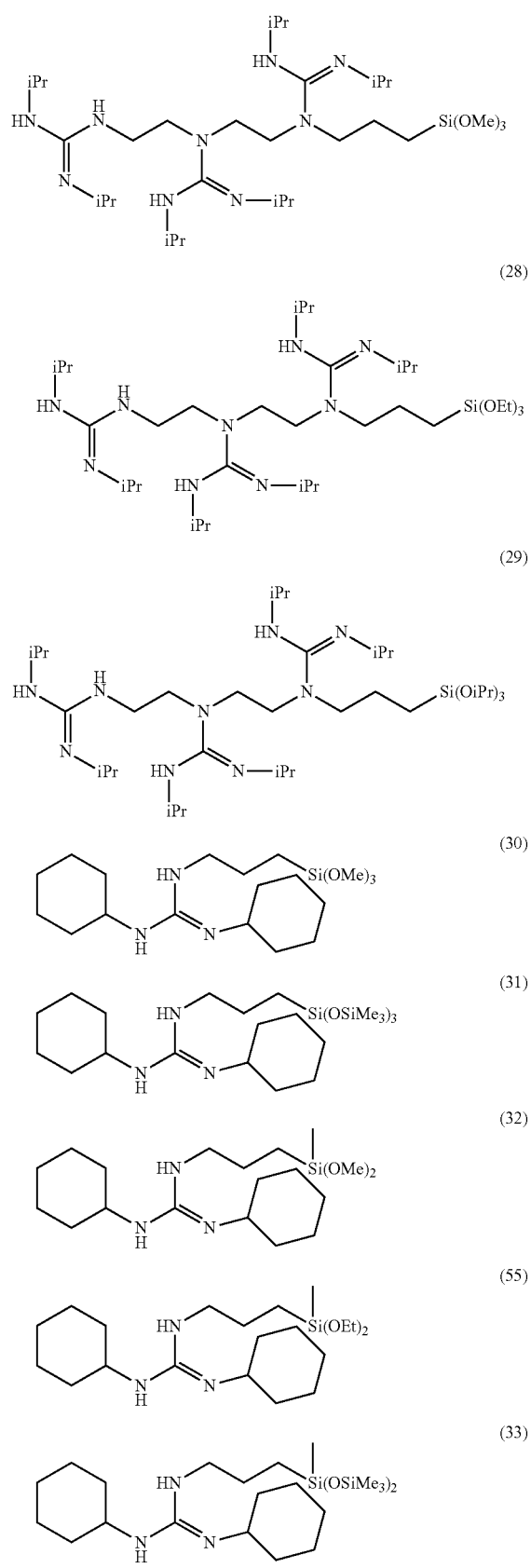

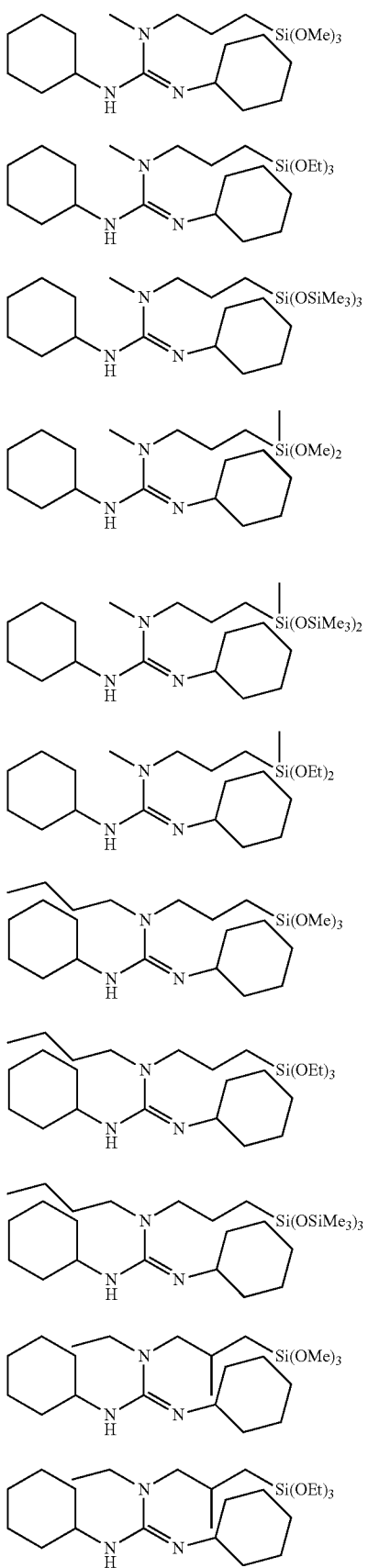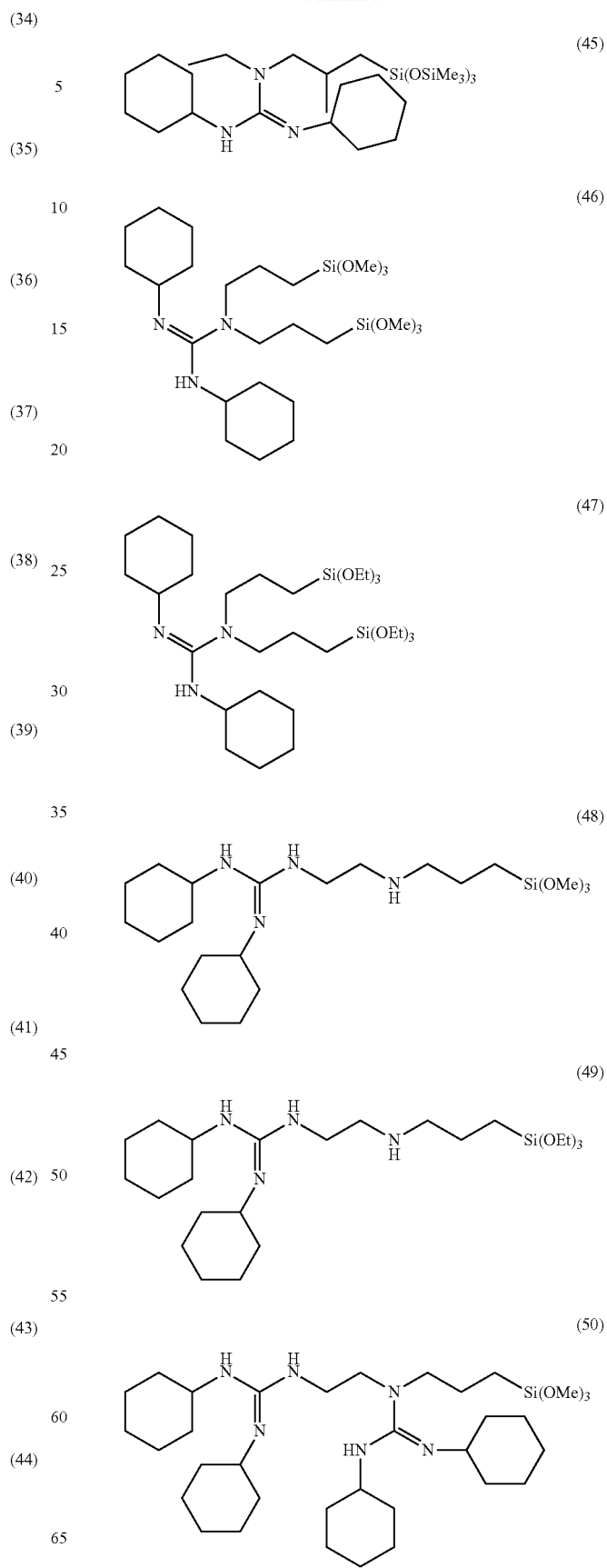

(51)
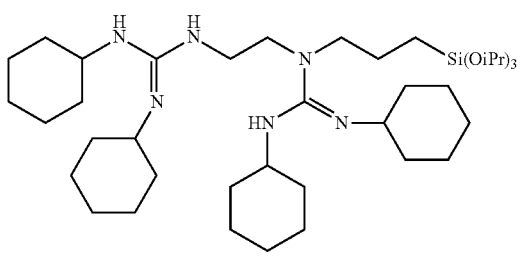

(52)
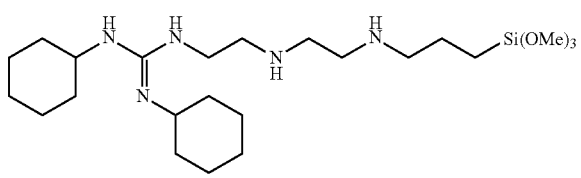

(53)
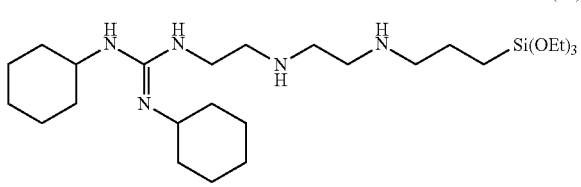

(54)
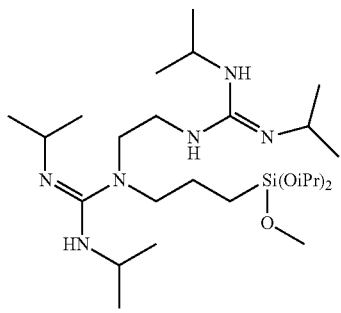

The compounds of formula (I) according to the invention are obtained, for example, according to a preparation process comprising the reaction of a carbodiimide of formula (II):

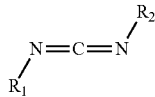  (II)

with a primary or secondary amine of formula (III):

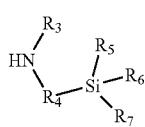  (III)

where $R_1$, $R_2$, $R_3$, $R_4$, $R_5$, $R_6$ and $R_7$ are as defined above.

The carbodiimides are generally obtained from ureas or thioureas, which are themselves obtained, for example, by reaction of a primary amine $R_1NH_2$ and an isocyanate $R_2NCO$. The carbodiimides are products that are known per se, which are commercially available.

The primary or secondary amine of formula (III), used in the present invention, comprises at least one silylated group. Such amines are known per se and are generally used in the field of silicones as adhesion promoters. The amines for which $R_5=R_6=R_7=OR_8$, or $R_5=Me$ and $R_6=R_7=OR_8$, or $R_5=R_6=Me$ and $R_7=OR_8$, where Me is the methyl group and $R_8$ is a methyl or ethyl group are commercially available.

The process according to the invention has the advantage of consisting of a simple and inexpensive synthesis, starting from common products.

According to the process according to the invention, the two products, carbodiimide and silylated amine, are heated in the presence or absence of a solvent.

According to one variant, the reaction of the carbodiimide of formula (II) with the amine of formula (III) is carried out without solvent. The reaction may take place at room temperature, but it is preferable to heat to a sufficient temperature dependent on the substitution of the amine (III). Thus, if $R_3=H$ it is desirable not to exceed a temperature of 100° C. and if $R_3 \neq H$ the reaction time is even shorter when the temperature is high. Thus, the temperature will be between 20 and 150° C., preferably between 70 and 130° C.

It is possible to use an excess of one or the other of the constituents: in the case of a volatile carbodiimide in excess, this excess will be removed at the end of the reaction, at the same time as the solvent when there is one, and if the amine is in excess, this will participate not only in the catalysis but also as an adhesion promoter. The excess may be from a few percent up to several equivalents, preferably between 10% and 1 equivalent. When the compound in deficit is completely consumed, the solvent, where appropriate, and optionally the excess of the other compound are evaporated, and the product formed, usually a not very viscous liquid, is used as is as a catalyst in polycondensation reactions.

The present invention also relates to the oligomers of the compounds described above, obtained by reaction of the groups bonded to the silicon, for example in the presence of moisture.

The present invention also relates to a guanidinium salt (IV) prepared by reacting a compound according to the invention and as defined above with an acid and preferably with a carboxylic acid.

The present invention also relates to an organopolysiloxane composition, characterized in that it comprises, on the one hand, a silicone base B capable of curing via polycondensation reaction into a silicone elastomer and, on the other hand, a catalytically effective amount of at least one polycondensation catalyst which is either a guanidinium salt (IV) according to the invention and as defined above, or a guanidine of formula (I) below:

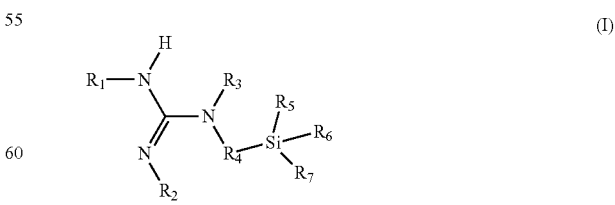  (I)

in which:

$R_1$ and $R_2$, which are identical or different, represent, independently of one another, a linear or branched monovalent alkyl group, a cycloalkyl group, a (cycloalkyl)alkyl group, the ring being substituted or unsubstituted and possibly comprising at least one heteroatom, an arylalkyl, fluoroalkyl, substituted or unsubstituted aryl or $R_{11}R_{12}R_{13}Si$ group, where $R_{11}$, $R_{12}$, and $R_{13}$ are linear or branched monovalent alkyl groups;

$R_3$ represents a hydrogen atom, a linear or branched monovalent alkyl group, a cycloalkyl group, an alkyl group substituted by a ring that is substituted or unsubstituted and that possibly comprises at least one heteroatom, an arylalkyl, fluoroalkyl, alkylamine, alkylguanidine or substituted or unsubstituted aryl group or an alkylalkoxysilane;

$R_4$ represents a linear or branched alkyl chain containing 1 to 50 atoms, preferably 1 to 20 atoms, some of them possibly being heteroatoms chosen from O, S and N;

$R_5$, $R_6$ et $R_7$, which are identical or different, represent, independently of one another, a linear or branched alkyl group, an aromatic group, an alkoxy group or a trialkylsilyloxy group of formula (I') below:

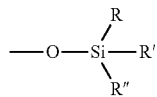
(I')

R, R' and R", which are identical or different, represent, independently of one another, a linear or branched $C_1$-$C_{12}$ alkyl group or an aromatic group;

on condition that if $R_3$ is a hydrogen atom, then $R_1$ and $R_2$ are not, either of them, a linear monovalent hydrocarbon-based group.

According to one preferred mode, the catalyst for polycondensation of the composition according to the invention is chosen from the compounds (1) to (55) as defined above.

The amount of compound of formula (I) is between 0.1 and 10% by weight of the total weight, preferably between 0.5 and 5%, whether it is a single-component or two-component preparation.

According to another of its aspects, one subject of the present invention is also an elastomer obtained by crosslinking and curing the composition described above.

The invention also relates to the use, as catalyst for the polycondensation reaction of organopolysiloxanes, of a guanidinium salt (IV) according to the invention and as defined above or of a compound of formula (I):

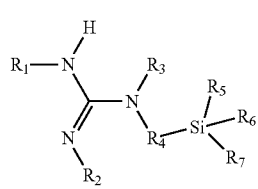
(I)

in which:

$R_1$ and $R_2$, which are identical or different, represent, independently of one another, a linear or branched monovalent alkyl group, a cycloalkyl group, a (cycloalkyl)alkyl group, the ring being substituted or unsubstituted and possibly comprising at least one heteroatom, an arylalkyl, fluoroalkyl, substituted or unsubstituted aryl or $R_{11}R_{12}R_{13}Si$ group, where $R_{11}$, $R_{12}$, and $R_{13}$ are linear or branched monovalent alkyl groups;

$R_3$ represents a hydrogen atom, a linear or branched monovalent alkyl group, a cycloalkyl group, an alkyl group substituted by a ring that is substituted or unsubstituted and that possibly comprises at least one heteroatom, an arylalkyl, fluoroalkyl, alkylamine, alkylguanidine or substituted or unsubstituted aryl group or an alkylalkoxysilane;

$R_4$ represents a linear or branched alkyl chain containing 1 to 50 atoms, preferably 1 to 20 atoms, some of them possibly being heteroatoms chosen from O, S and N;

$R_5$, $R_6$ and $R_7$, which are identical or different, represent, independently of one another, a linear or branched alkyl group, an aromatic group, an alkoxy group or a trialkylsilyloxy group of formula (I') below:

(I')

R, R' and R", which are identical or different, represent, independently of one another, a linear or branched $C_1$-$C_{12}$ alkyl group or an aromatic group; and on condition that if $R_3$ is a hydrogen atom, then $R_1$ and $R_2$ are not, either of them, a linear monovalent hydrocarbon-based group.

The guanidinium salt (IV) may be obtained by addition of a carboxylic acid (for example a linear or branched $C_2$-$C_{15}$ carboxylic acid) to the compound of formula (I) in the presence or absence of a solvent.

The catalysts in accordance with the present invention are nontoxic, unlike the alkyltin-based catalysts. Furthermore, they make it possible to achieve, both under single-component and two-component conditions, silicone polycondensation rates that are as high or even better than those obtained with these alkyltin-based catalysts.

Description of the Silicone Base B:

The silicone bases used in the present invention that crosslink and cure via polycondensation reactions are well known. These bases are described in detail in particular in numerous patents and they are commercially available.

These silicone bases may be single-component bases, that is to say bases that are packaged in a single package, and stable during storage, in the absence of moisture, which can be cured in the presence of moisture, in particular moisture provided by the ambient air or by water generated within the base during the use thereof.

Apart from single-component bases, use may be made of two-component bases, that is to say bases that are packaged in two packages, which cure as soon as the polycondensation catalyst according to the invention is incorporated. They are packaged, after incorporation of the catalyst, in two separate fractions, one of the fractions possibly containing, for example, only the catalyst according to the invention or a mixture with the crosslinking agent.

The silicone base B used to produce the composition according to the invention may comprise:
- at least one polyorganosiloxane oil C capable of crosslinking via polycondensation into an elastomer;
- optionally at least one crosslinking agent D;
- optionally at least one adhesion promoter E; and
- optionally at least one siliceous, organic and/or non-siliceous mineral filler F.

The polyorganosiloxane oil C is preferably an α,ω-dihydroxypolydiorganosiloxane polymer, with a viscosity between 50 and 5 000 000 mPa·s at 25° C. and the crosslinking agent D is preferably an organosilicon compound bearing more than two hydrolyzable groups bonded to the silicon atoms per molecule. The polyorganosiloxane oil C may also be functionalized at its ends by hydrolyzable radicals obtained by condensation of a precursor bearing hydroxyl functional groups with a crosslinking silane bearing hydrolyzable radicals.

As the crosslinking agent (D), mention may be made of: silanes of the following general formula:

in which the symbols $R^2$, which are identical or different, represent alkyl radicals having from 1 to 8 carbon atoms, such as methyl, ethyl, propyl, butyl, pentyl or 2-ethylhexyl radicals, $C_3$-$C_6$ oxyalkylene radicals, the symbol $R^1$ represents a linear or branched, saturated or unsaturated, aliphatic hydrocarbon-based group, a saturated or unsaturated and/or aromatic, monocyclic or polycyclic carbocyclic group, and k is equal to 0, 1 or 2; and the partial hydrolysis products of this silane.

As examples of $C_3$-$C_6$ alkoxyalkylene radicals, mention may be made of the following radicals:

$CH_3OCH_2CH_2$—
$CH_3OCH_2CH(CH_3)$—
$CH_3OCH(CH_3)CH_2$—
$C_2H_5OCH_2CH_2CH_2$—

The symbol $R^1$ represents a $C_1$-$C_{10}$ hydrocarbon-based radical that encompasses:
  $C_1$-$C_{10}$ alkyl radicals such as methyl, ethyl, propyl, butyl, pentyl, 2-ethylhexyl, octyl or decyl radicals;
  vinyl and allyl radicals; and
  $C_5$-$C_8$ cycloalkyl radicals such as phenyl, tolyl and xylyl radicals.

The crosslinking agents D are products that are available on the silicones market; furthermore, their use in room-temperature curing compositions is known; it occurs in particular in French patents FR-A-1 126 411, FR-A-1 179 969, FR-A-1 189 216, FR-A-1 198 749, FR-A-1 248 826, FR-A-1 314 649, FR-A-1 423 477, FR-A-1 432 799 and FR-A-2 067 636.

Preference is more particularly given, among the crosslinking agents D, to alkyltrialkoxysilanes, alkyl silicates and alkyl polysilicates, in which the organic radicals are alkyl radicals having from 1 to 4 carbon atoms.

As other examples of crosslinking agents D that may be used, mention is more particularly made of the following silanes:
  propyltrimethoxysilane;
  methyltrimethoxysilane;
  ethyltrimethoxysilane;
  vinyltriethoxysilane;
  methyltriethoxysilane;
  propyltriethoxysilane;
  tetraethoxysilane;
  tetrapropoxysilane;
  1,2-bis(trimethoxysilyl)ethane;
  1,2-bis(triethoxysilyl)ethane; and
  tetraisopropoxysilane,
  or else: $CH_3Si(OCH_3)_3$; $C_2H_5Si(OC_2H_5)_3$; $C_2H_5Si(OCH_3)_3CH_2=CHSi(OCH_3)_3$; $CH_2=CHSi(OCH_2CH_2OCH_3)_3C_6H_5Si(OCH_3)_3$; $[CH_3][OCH(CH_3)CH_2OCH_3]Si[OCH_3]_2Si(OCH_3)_4$; $Si(OC_2H_5)_4$; $Si(OCH_2CH_2CH_3)_4$; $Si(OCH_2CH_2CH_2CH_3)_4Si(OC_2H_4OCH_3)_4$; $CH_3Si(OC_2H_4OCH_3)_3$; $ClCH_2Si(OC_2H_5)_3$.

As other examples of crosslinking agent D, mention may be made of ethyl polysilicate or n-propyl polysilicate.

Use is generally made of 0.1 to 60 parts by weight of crosslinking agent D per 100 parts by weight of polyorganosiloxane C capable of crosslinking via polycondensation to an elastomer.

Thus the composition according to the invention may comprise at least one adhesion promoter E such as, for example, the organosilicon compounds bearing both:
  (1) one or more hydrolyzable groups bonded to the silicon atom, and
  (2) one or more organic groups substituted with radicals comprising a nitrogen atom or chosen from the group of (meth)acrylate, epoxy and alkenyl radicals, and more preferably still from the group constituted by the following compounds, taken alone or as a mixture:
  vinyltrimethoxysilane (VTMO);
  3-glycidoxypropyltrimethoxysilane (GLYMO);
  methacryloxypropyltrimethoxysilane (MEMO);
  $[H_2N(CH_2)_3]Si(OCH_2CH_2CH_3)_3$;
  $[H_2N(CH_2)_3]Si(OCH_3)_3$;
  $[H_2N(CH_2)_3]Si(OC_2H_5)_3$;
  $[H_2N(CH_2)_4]Si(OCH_3)_3$;
  $[H_2NCH_2CH(CH_3)CH_2CH_2]SiCH_3(OCH_3)_2$;
  $[H_2NCH_2]Si(OCH_3)_3$;
  $[n-C_4H_9-HN-CH_2]Si(OCH_3)_3$;
  $[H_2N(CH_2)_2NH(CH_2)_3]Si(OCH_3)_3$;
  $[H_2N(CH_2)_2NH(CH_2)_3]Si(OCH_2CH_2OCH_3)_3$;
  $[CH_3NH(CH_2)_2NH(CH_2)_3]Si(OCH_3)_3$;
  $[H(NHCH_2CH_2)_2NH(CH_2)_3]Si(OCH_3)_3$;

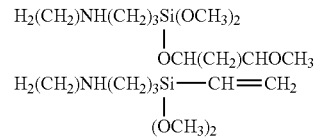

or polyorganosiloxane oligomers containing such organic groups at a content greater than 20%.

For the single-component and two-component bases, use is made, as the mineral fillers F, of very finely divided products, the average particle diameter of which is less than 0.1 μm. These fillers include fumed silicas and precipitated silicas; their BET specific surface area is generally greater than 40 m²/g. These fillers may also be in the form of more coarsely divided products, having an average particle diameter greater than 0.1 μm. As examples of such fillers, mention may be made of ground quartz, diatomaceous silicas, calcium carbonate, calcined clay, rutile-type titanium oxide, iron, zinc, chromium, zirconium or magnesium oxides, the various forms of alumina (hydrated or unhydrated), boron nitride, lithopone, barium metaborate, barium sulfate and glass microbeads; their specific surface area is generally less than 30 m²/g.

These fillers may have been surface-modified by treatment with the various organosilicon compounds customarily employed for this purpose. Thus, these organosilicon compounds may be organochlorosilanes, diorganocyclopolysiloxanes, hexaorganodisiloxanes, hexaorganodisilazanes or diorganocyclopolysilazanes (French patents FR-A-1 126 884, FR-A-1 136 885 and FR-A-1 236 505, and British patent GB-A-1 024 234). The treated fillers contain, in most cases, from 3 to 30% of their weight of organosilicon compounds. The fillers may be constituted of a mixture of several types of fillers of different particle size; thus, for example, they may be constituted of 30 to 70% of finely divided silicas with a BET specific surface area greater than 40 m²/g and of 70 to 30% of more coarsely divided silicas with a specific surface area less than 30 m²/g.

The purpose of introducing fillers is to give good mechanical and rheological properties to the elastomers that result from the curing of the compositions according to the invention.

In combination with these fillers, use may be made of mineral and/or organic pigments and also agents that improve the thermal resistance (salts and oxides of rare-earth elements such as ceric oxides and hydroxides) and/or the fire resistance of the elastomers. For example, it is possible to use the cocktails of oxides described in international application WO 98/29488. Mention may be made, among the agents for improving the fire resistance, of halogenated organic derivatives, organic phosphorus derivatives, platinum derivatives, such as chloroplatinic acid (its reaction products with alkanols or ethers), or platinous chloride-olefin complexes. These pigments and agents together represent at most 20% of the weight of the fillers.

Other customary auxiliary agents and additives may be incorporated into the composition according to the invention; these are chosen as a function of the applications in which said compositions are used.

The silicone base used to produce the composition according to the invention may comprise:
- 100 parts of polyorganosiloxane oil C capable of crosslinking via polycondensation into an elastomer;
- 0 to 20 parts of a crosslinking agent D;
- 0 to 20 parts of an adhesion promoter E; and
- 0 to 50 parts of filler F.

In addition to the main constituents, nonreactive linear polyorganosiloxane polymers G may be introduced with the intention of acting on the physical characteristics of the compositions in accordance with the invention and/or on the mechanical properties of the elastomers resulting from the curing of these compositions.

These nonreactive linear polyorganosiloxane polymers G are well known; they comprise more especially: $\alpha,\omega$-bis(triorganosiloxy)diorganopolysiloxane polymers with viscosities of at least 10 mPa·s at 25° C. formed essentially of diorganosiloxy units and of at least 1% of monoorganosiloxy and/or siloxy units, the organic radicals bonded to the silicon atoms being chosen from the methyl, vinyl and phenyl radicals, 60% at least of these organic radicals being methyl radicals and 10% at most being vinyl radicals. The viscosity of these polymers can reach several tens of millions of mPa·s at 25° C.; they therefore include oils with a fluid to viscous appearance and soft to hard gums. They are prepared according to the usual techniques described more specifically in French patents FR-A-978 058, FR-A-1 025 150, FR-A-1 108 764 and FR-A-1 370 884. Use is preferably made of $\alpha,\omega$-bis (trimethylsiloxy)dimethylpolysiloxane oils with a viscosity ranging from 10 mPa·s to 1000 mPa·s at 25° C. These polymers, which act as plasticizers, can be introduced in a proportion of at most 70 parts, preferably of 5 to 20 parts, per 100 parts of the polyorganosiloxane oil C capable of crosslinking via polycondensation.

The compositions according to the invention can in addition advantageously comprise at least one silicone resin H. These silicone resins are branched organopolysiloxane polymers which are well known and which are available commercially. They have, per molecule, at least two different units chosen from those of formula $R'''_3SiO_{1/2}$ (M unit), $R'''_2SiO_{2/2}$ (D unit), $R'''SiO_{3/2}$ (T unit) and $SiO_{4/2}$ (Q unit). The $R'''$ radicals are identical or different and are chosen from linear or branched alkyl radicals or vinyl, phenyl or 3,3,3-trifluoropropyl radicals. Preferably, the alkyl radicals have from 1 to 6 carbon atoms inclusive. More particularly, mention may be made, as alkyl R radicals, of methyl, ethyl, isopropyl, tert-butyl and n-hexyl radicals. These resins are preferably hydroxylated and have, in this case, a weight content of hydroxyl groups of between 5 and 500 meq/100 g.

Mention may be made, as examples of resins, of MQ resins, MDQ resins, TD resins and MDT resins.

In order to manufacture the compositions according to the invention it is necessary, in the case of the single-component compositions, to use equipment that makes it possible to intimately mix the various fundamental constituents in a moisture-free environment, with or without a supply of heat, optionally added to which constituents are the aforementioned adjuvants and additives. All these ingredients may be loaded into the equipment in any order of introduction. Thus, it is possible to firstly mix the organopolysiloxane oils C and the fillers F and then to add to the paste obtained the crosslinkers D, the compounds E and the catalyst according to the invention. It is also possible to mix the oils C, the crosslinkers D, the compounds E and the fillers F and to subsequently add the catalyst according to the invention. During these operations, the mixtures may be heated at a temperature within the range of 50-180° C. under atmospheric pressure or under a reduced pressure in order to promote the removal of volatile materials.

The single-component compositions according to the invention, used as they are, that is to say undiluted, or in the form of dispersions in diluents, are stable during storage in the absence of water and cure at low temperatures (after removal of solvents in the case of dispersions) in the presence of water to form elastomers.

After the deposition of the compositions as they are, onto solid substrates, in a humid atmosphere, it is observed that a process of curing into elastomers occurs, it takes place from the outside to the inside of the mass deposited. A skin forms first at the surface, then the crosslinking continues in depth. The complete formation of the skin, which results in a tack-free feel of the surface, requires a period of time of a few minutes; this period of time depends on the degree of relative humidity of the atmosphere surrounding the compositions and on the crosslinkability of the latter.

Furthermore, the in-depth curing of the deposited layers, which must be sufficient to allow the demolding and handling of the elastomers formed, requires a longer period of time. Indeed, this period of time depends not only on the factors mentioned above for the formation of the tack-free feel but also on the thickness of the deposited layers, which thickness generally lies between 0.5 mm and several centimeters. The single-component compositions may be used for multiple applications such as jointing in the construction industry, assembling the most diverse materials (metals, plastics, natural and synthetic rubbers, wood, board, earthenware, brick, ceramic, glass, stone, concrete, masonry units), insulating electrical conductors, the potting of electronic circuits, or the preparation of molds used for manufacturing articles made of synthetic resins or foams.

The manufacture of the two-component compositions according to the invention is also carried out by mixing various constituents in suitable equipment. In order to obtain homogeneous compositions, it is preferable to firstly mix the polymers A with the fillers C; the whole mixture may be heated for at least 30 minutes at a temperature above 80° C., so as to complete the wetting of the fillers by the oils. To the mixture obtained, preferably brought to a temperature below 80° C., for example of around room temperature, may be added the other constituents, that is to say the crosslinking agents, the catalyst and optionally various additives and adjuvants and even water.

The compositions in accordance with the invention may be employed for multiple applications, such as jointing and/or bonding in the construction industry or the transportation industry (e.g.: automobile, aerospace, railroad, maritime and aeronautical industries), assembling the most diverse materials (metals, plastics, natural and synthetic rubbers, wood, boards, polycarbonate, earthenware, brick, ceramic, glass, stone, concrete and masonry units), insulating electrical conductors, the potting of electronic circuits, and the preparation of molds used for manufacturing articles made of synthetic resins or foams.

Thus, another subject of the invention consists of a two-component system that is a precursor of the organopolysiloxane composition according to the invention and as defined above and that can be vulcanized to a silicone elastomer via polycondensation reactions and characterized in that it is in two separate parts P1 and P2 intended to be mixed in order to form said composition, and in that one of these parts comprises the catalyst according to the invention and as defined above as a catalyst for the polycondensation reaction of organopolysiloxanes and the crosslinking agent D, whilst the other part is free of the aforementioned species and comprises:

100 parts by weight of the polyorganosiloxane oil(s) C capable of crosslinking via polycondensation into an elastomer;

from 0.001 to 10 part(s) by weight of water.

Another subject of the invention also consists of a single-component polyorganosiloxane composition that is stable during storage in the absence of moisture and that crosslinks, in the presence of water, into an elastomer, characterized in that it comprises:

at least one crosslinkable linear polyorganopolysiloxane that has functionalized ends of alkoxy, oxime, acyl and/or enoxy type, preferably alkoxy type;

a filler; and the catalyst of the polycondensation reaction according to the invention and as defined above.

Single-component bases are described in detail, for example, in patents EP 141 685, EP 147 323, EP 102 268, EP 21 859, FR 2 121 289 and FR 2 121 631, cited as reference.

It is possible to add, to these single-component bases, adhesion promoters E chosen, for example, from organosilicon compounds simultaneously bearing, on the one hand, organic groups substituted by radicals chosen from the group of amino, ureido, isocyanate, epoxy, alkenyl, isocyanurate, hydantoyl, guanidino and mercaptoester radicals and, on the other hand, hydrolyzable groups, in general alkoxy groups bonded to the silicon atoms. Examples of such adhesion agents are described in U.S. Pat. No. 3,517,001, U.S. Pat. No. 4,115,356, U.S. Pat. No. 4,180,642, U.S. Pat. No. 4,273,698, U.S. Pat. No. 4,356,116 and in European patents EP 31 996 and EP 74 001.

Two-component bases are described in detail, for example, in patents EP 118 325, EP 117 772, EP 10 478, EP 50 358, EP 184 966, U.S. Pat. No. 3,801,572 and U.S. Pat. No. 3,888,815 cited as reference.

The final subject of the invention consists of an elastomer obtained by crosslinking and curing of the two-component system according to the invention and as described above, or of the composition according to the invention and as described above.

Other advantages and features of the present invention will appear on reading the following examples that are given by way of illustration and that are in no way limiting.

EXAMPLES 1. 1,2-diisopropyl-3-(3-(trimethoxysilyl)propyl) guanidine (1)

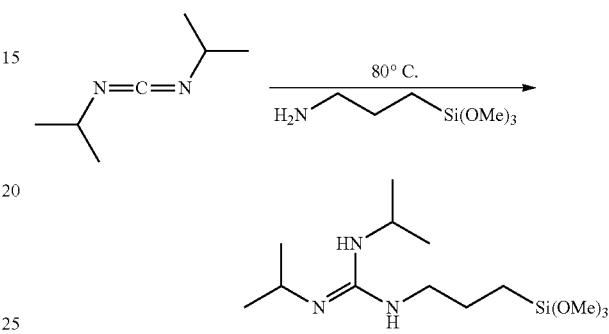

A mixture of 11.74 g of (3-(trimethoxysilyl)propyl)amine (0.0654 mol) and of 9.9 g of diisopropylcarbodiimide (0.0785 mol, 20% excess) was heated for 6 h 30 min at 80° C. Analysis by GC then showed an amine conversion of greater than 97%. The final colorless mixture was evaporated to dryness at 100° C. under 2 mbar for 2 h to give 22.5 g of a colorless, low-viscosity liquid corresponding to the expected guanidine.

$^1$H NMR/CDCl$_3$ (ppm): 0.69 (2H, m), 1.12 (12H, d), 1.63 (2H, quint.), 2.99 (2H, t), 3.48 (11H, broad s—the shift of the isopropyl protons overlaps with the methoxy protons)

2. 1-(3-(diethoxy(methyl)silyl)propyl)-2,3-diisopropylguanidine (5)

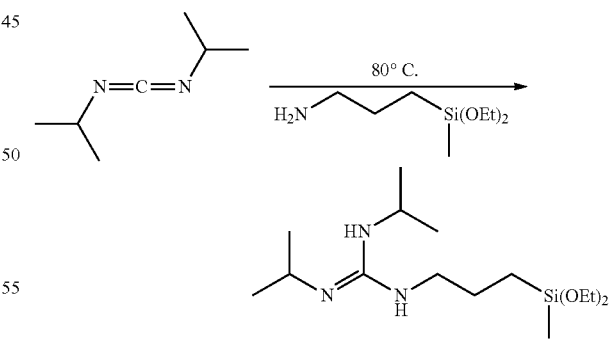

A mixture of 28.94 g of 3-(diethoxy(methyl)silyl)propylamine (0.151 mol, 20% excess) and of 15.9 g of diisopropylcarbodiimide (0.126 mol) was heated for 9 h at 80° C. (carbodiimide conversion of 97.3%).

The final colorless mixture was devolatilized at 100° C. under 2 mbar for 2 h to give 44 g of a colorless, low-viscosity liquid corresponding to a mixture of the expected guanidine and of the silylated amine in excess (9.8 wt %).

¹H NMR/CDCl₃ (ppm) of the silylated guanidine: 0.0 (3H, s), 0.54 (2H, m), 1.01 (12H, d), 1.1 (6H, t), 1.49 (2H, m), 2.88 (2H, t), 3.46 (2H, m), 3.64 (4H, quad.).

3. 2,3-diisopropyl-1-methyl-1-(3-(trimethoxysilyl)propyl)guanidine (7)

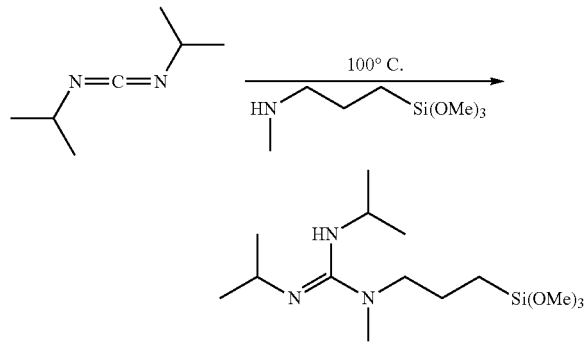

A mixture of 60.5 g of N-methyl-(3-(trimethoxysilyl)propyl)amine (0.313 mol) and of 47.6 g of diisopropylcarbodiimide (0.376 mol, 20% excess) was heated for 3 h 30 min at 100° C. (amine conversion of greater than 99%). The final colorless mixture was devolatilized at 100° C. under 2 mbar for 2 h to give 99.5 g of a colorless, low-viscosity liquid corresponding to the expected guanidine.

¹H NMR/CDCl₃ (ppm): 0.5 (2H, m), 1.0 (12H, 2 d), 1.53 (2H, quint.), 2.61 (3H, s), 2.98 (2H, t), 3.21 (1H, sept), 3.32 (1H, sept), 3.48 (9H, s).

4. 2,3-diisopropyl-1-methyl-1-(3-(methyldimethoxysilyl)propyl)guanidine (10)

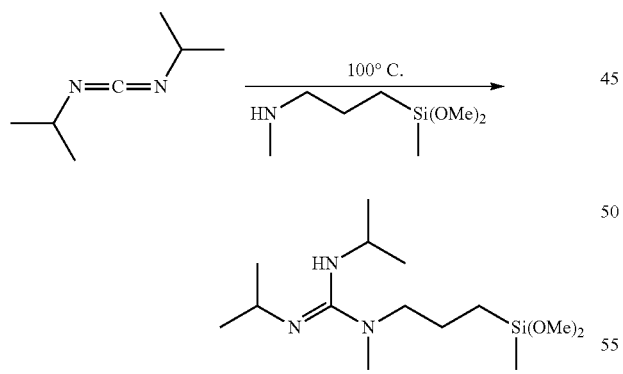

A mixture of 27 g of N-methyl-(3-(methyldimethoxysilyl)propyl)amine (0.152 mol, 20% excess) and of 16 g of diisopropylcarbodiimide (0.127 mol) was heated for 8 h at 100° C. (carbodiimide conversion of 98%). The final colorless mixture was devolatilized at 100° C. under 2 mbar for 2 h to give 39.3 g of a colorless, low-viscosity liquid corresponding to the expected guanidine, containing 2 wt % of the initial amine.

¹H NMR/CDCl₃ (ppm) of the guanidine: 0.0 (3H, s), 0.46 (2H, m), 0.97 (12H, m), 1.46 (2H, m), 2.58 (3H, s), 2.95 (2H, t), 3.18 (1H, m), 3.28 (1H, m), 3.40 (6H, s).

5. 1-butyl-2,3-diisopropyl-1-(3-(trimethoxysilyl)propyl)guanidine (13)

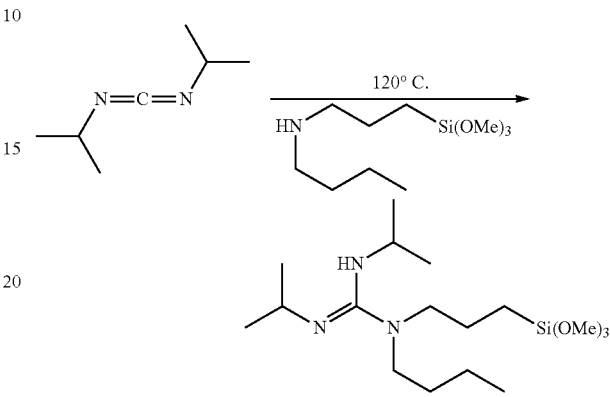

A mixture of 45 g of N-butyl-(3-(trimethoxysilyl)propyl)amine (0.191 mol) and of 28.95 g of diisopropylcarbodiimide (0.229 mol, 20% excess) was heated for 20 h at 120° C. (amine conversion of 93%). The final colorless mixture was devolatilized at 120° C. under 1 mbar for 2 h to give 67 g of a colorless, low-viscosity liquid corresponding to the expected guanidine, containing 4 wt % of the initial amine.

¹H NMR/CDCl₃ (ppm) of the guanidine: 0.58 (2H, m), 0.88 (3H, t), 1.07 (12H, 2 d), 1.26 (2H, sext.), 1.44 (2H, quint.), 1.58 (2H, quint.), 3.06 (4H, t), 3.30 (1H, m), 3.41 (1H, m), 3.55 (9H, s).

6. 1,1-bis(3-(trimethoxysilyl)propyl)-2,3-diisopropylguanidine (19)

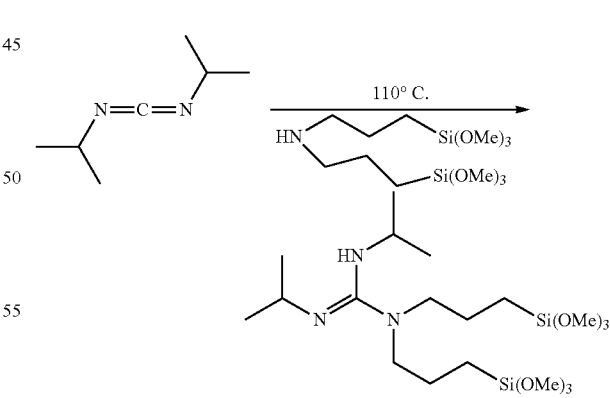

A mixture of 30.84 g of bis(3-(trimethoxysilyl)propyl)amine (0.0903 mol) and of 13.68 g of diisopropylcarbodiimide (0.1084 mol, 20% excess) was heated for 31 h at 110° C. (amine conversion of 94%). The final colorless mixture was devolatilized at 100° C. under 2 mbar for 2 h to give 42 g of a colorless, low-viscosity liquid corresponding to the expected guanidine, containing 4% of the initial amine.

¹H NMR/CDCl₃ (ppm) of the guanidine: 0.56 (4H, m), 1.07 (12H, m), 1.57 (4H, m), 3.05 (4H, t), 3.30 (1H, sept.), 3.43 (1H, sept.), 3.54 (18H, s.)

7. 2,3-dicyclohexyl-1-methyl-1-(3-(trimethoxysilyl) propyl)guanidine (34)

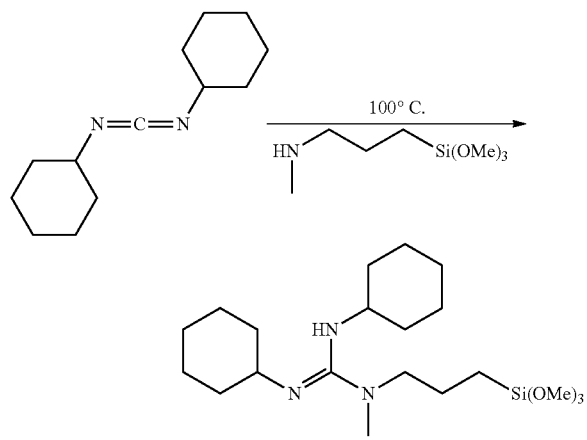

A mixture of 23.23 g of N-methyl-(3-(trimethoxysilyl)propyl)amine (0.12 mol, 20% excess) and of 20.65 g of dicyclohexylcarbodiimide (0.1 mol) was heated for 6 h at 100° C. (carbodiimide conversion of 94%). The final colorless mixture was devolatilized at 100° C. under 2 mbar for 2 h to give 41.3 g of a colorless, moderately viscous liquid corresponding to the expected guanidine, containing 6% of the initial amine.

¹H NMR/CDCl₃ (ppm) of the guanidine: 0.58 (2H, m), 1-1.4 (10H, m), 1.5-2 (12H, m), 2.69 (3H, s), 2.8-3.1 (2H, m), 3.07 (2H, t), 3.56 (9H, s).

8. 2,3-diisopropyl-1-[(3-ethoxysilyl)propyl]-1-[2-[(2, 3-diisopropyl)guanidino]ethyl]guanidine (54)

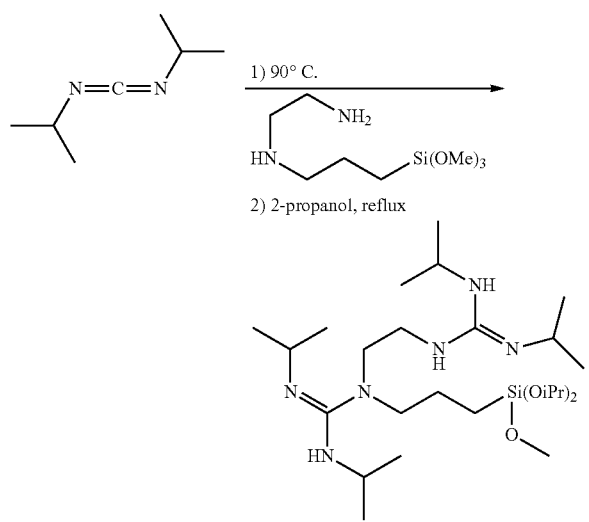

A mixture of 20.01 g of N-[3-(trimethoxysilyl)propyl]ethylenediamine (0.09 mol) and of 27.26 g of diisopropylcarbodiimide (0.216 mol, 20% excess) was heated for 8 h at 90° C. and for 72 h at 70° C. (conversion: 100% for diamine, 93% for monoguanidine intermediates).

The final colorless mixture was devolatilized at 100° C. under 2 mbar for 2 h to give 41.6 g of a very viscous liquid which crystallized after several minutes. The solid was taken up with 50 ml of 2-propanol, and the solution was heated to reflux, while distilling the methanol formed, for 3 h, then evaporated to dryness again to give a moderately viscous liquid corresponding to the expected guanidine, with SiOMe(OiPr)₂ average substitution.

9. Synthesis of 2,3-diisopropyl-1-methyl-1-(3-(bis (trimethylsilyloxy)methylsilyl)propyl) guanidine (12)

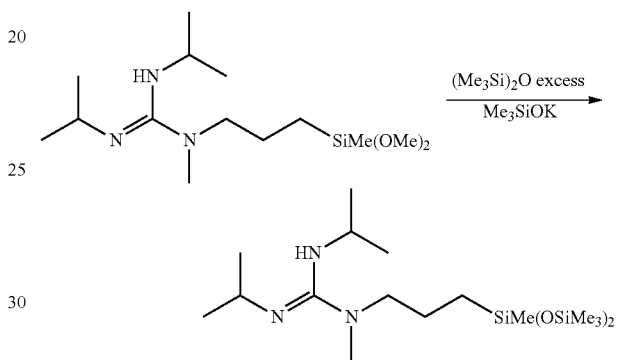

A mixture of 2 g of 2,3-diisopropyl-1-methyl-1-(3-(methyldimethoxysilyl)propyl)guanidine, 10 g of hexamethyldisiloxane and 50 mg of potassium silanolate was heated at 100° C. for 24 h. After cooling, the cloudy medium was diluted with heptane. The suspension was filtered then evaporated to dryness to give 2.5 g of a colorless, nonviscous liquid. Analysis by ¹H NMR showed that the exchange had been carried out to more than 90%.

10. Single-Component Compositions 10.1. Paste Test—Vinyltrimethoxysilane Crosslinker The paste used was prepared as follows: added, with stirring, to a mixture of 3464 g of an α,ω-dihydroxylated oil with a viscosity of 20 000 centipoise containing 0.066% of OH, and of 120 g of vinyltrimethoxysilane were 16 g of a 2 wt % solution of lithium hydroxide in methanol, then, after 5 min, 400 g of AE55 fumed silica were added. The mixture was devolatilized under vacuum then stored in a moisture-free environment.

For each test, the catalyst tested was mixed with 50 g of this paste, then the catalytic potential was evaluated in 3 ways (see the tables of results below):

the skin-over time (SOT), time at the end of which surface crosslinking is observed, on a 2 mm film;

the persistence of a tacky feel at 48 h;

the hardness (Shore A hardness) of a 6 mm thick bead under controlled conditions (23° C. and 50% relative humidity) and over increasing times (2, 3, 4, 7 and 14 days). The high temperature stability was also evaluated by hardness measurements carried out on the bead after 7 days at room temperature followed by 7 days at 100° C.

NB: The Shore hardness was measured on a 6 mm bead. In the tables of results the symbol ">" corresponds to the hardness values measured on the upper part of the bead and the symbol "<" corresponds to the hardness values measured on the lower part of the bead that is less exposed to the ambient air than the upper part.

Various catalysts according to the invention were tested.

By way of comparison, as above, the following were also tested:
a tin-based catalyst: dibutyltin dilaurate (DBTDL);
1,1,3,3-tetramethylguanidine; and
a catalyst described in U.S. Pat. No. 4,248,993 which is 1,1,3,3-tetramethyl-(3-triethoxysilyl)propyl)guanidine having the following formula:

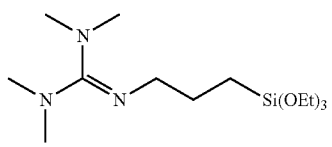

The results are given in table I below.

TABLE I

| | | | | Tacky | Shore A hardness over 6 mm | | | | | | | | | | |
|---|---|---|---|---|---|---|---|---|---|---|---|---|---|---|---|
| | | mol/ | SOT | feel | | | | | | | | | | 7 d RT + | |
| Ref- | | Sn | stick | at | 2 d | | 3 d | | 4 d | | 7 d | | 14 d | | 7 d 100° C. | |
| erence | Product | (1) | wt % | min | 48 h | > | < | > | < | > | < | > | < | > | < | > | < |
| Comparative | DBTDL | 1 | 1.1 | 20 | no | 34 | 26 | 35 | 31 | 35 | 32 | 33 | 30 | 34 | 31 | 33 | 30 |
| Comparative | 1,1,3,3 tetramethylguanidine | 4 | 0.6 | 2 | yes | 2 | 1 | 2 | 1 | | | 4 | 3 | 2 | 1 | 1 | 1 |
| Comparative | [structure] | 5.7 | 2.6 | 2 | no | 20 | 3 | 24 | 11 | 24 | 13 | 26 | 18 | 20 | 15 | 17 | 10 |
| 1 | [structure] | 3 | 1.3 | 1 | no | 30 | 16 | 31 | 20 | 32 | 21 | 32 | 22 | 34 | 23 | 22 | 15 |
| 5 | [structure] | 4 | 1.8 | 1 | no | 27 | 18 | 27 | 20 | | | 30 | 20 | 30 | 20 | 18 | 12 |
| 7 | [structure] | 3 | 1.3 | 1 | no | 29 | 16 | 31 | 21 | 33 | 21 | 32 | 24 | 31 | 24 | 30 | 23 |
| | | 2 | 0.9 | 1 | no | 27 | 10 | 30 | 16 | 31 | 19 | 30 | 22 | 30 | 22 | 31 | 22 |
| | | 1.5 | 0.7 | 2 | yes | 20 | 5 | 25 | 10 | 27 | 15 | 29 | 19 | 33 | 22 | 32 | 21 |
| 10 | [structure] | 1.5 | 0.6 | 2 | no | 30 | 7 | 34 | 14 | 34 | 17 | 36 | 22 | 36 | 25 | 34 | 24 |
| 13 | [structure] | 3 | 1.5 | 2 | no | 33 | 20 | 33 | 25 | 33 | 26 | 33 | 26 | 31 | 26 | 31 | 26 |

TABLE I-continued

| Reference | Product | mol/Sn (1) | SOT stick wt % | Tacky feel at min | Shore A hardness over 6 mm | | | | | | | | | | 7 d RT + 7 d 100° C. | |
|---|---|---|---|---|---|---|---|---|---|---|---|---|---|---|---|---|
| | | | | | 2 d | | 3 d | | 4 d | | 7 d | | 14 d | | | |
| | | | | 48 h | > | < | > | < | > | < | > | < | > | < | > | < |
| 19 | [structure: guanidine with Si(OMe)₃ groups] | 4 | 2.7 | 1 no | 39 | 7 | 40 | 16 | | | 40 | 19 | 40 | 20 | 40 | 20 |
| 54 | [structure: bis-guanidine with Si(OMe)(OiPr)₂] | 1 | 0.8 | 1 no | 29 | 21 | 30 | 23 | 29 | 22 | 31 | 24 | 33 | 25 | 27 | 22 |
| 12 | [structure: guanidine with Si(OSiMe₃)₂] | 1.5 | 0.9 | 3 no | 35 | 26 | 35 | 27 | 35 | 28 | 35 | 28 | 36 | 29 | 36 | 29 |
| | | 0.75 | 0.4 | 6 no | 32 | 15 | 33 | 24 | 34 | 26 | 34 | 27 | 37 | 29 | 35 | 28 |

(1) Indicates, for each example, the [catalyst]/[Sn]$_{comparative\ 1}$ ratio.

Although dibutyltin dilaurate is a good catalyst as regards the crosslinking kinetics (hardness), the skin-over time is 5 to 10 times longer compared to those given by guanidines in general. On the other hand, 1,1,3,3-tetramethylguanidine does not enable crosslinking of the silicone oil in depth, even at a molar concentration higher than the silylated guanidines according to the invention. As regards the comparative catalyst of pentasubstituted structure, 1,1,3,3-tetramethyl-(3-triethoxysilyl)propyl)guanidine, which was added at a 50% higher molar concentration, the crosslinking kinetics are much lower than those of the silylated guanidines according to the invention, in particular lack of in-depth crosslinking and the 2 mm film tearing at 48 h.

These results show that the nontoxic catalysts according to the invention result in faster catalysis than the tin-based catalysts and especially than the tetramethylguanidine structure. The catalysts according to the invention can therefore advantageously replace the existing catalysts. Moreover, the skin-over time may be extended by reducing the catalyst concentration on condition that the silane functional group is rendered sufficiently unreactive (reference 12), with hardness kinetics comparable to those obtained with dialkyltin compounds. The elastomers obtained are particularly heat stable in the case of the tetrasubstituted guanidines (references 7, 10, 13, 19 and 12).

10.2. Paste Test—Vinyltriethoxysilane Crosslinker

The paste used was prepared as follows: added, with stirring, to a mixture of 857.5 g of an α,ω-dihydroxylated oil with a viscosity of 20 000 centipoise containing 0.066% of OH, and of 38.5 g of vinyltriethoxysilane were 4 g of a 4 wt % solution of lithium hydroxide in methanol, then, after 20 min, 100 g of AE55 fumed silica were added. The mixture was devolatilized under vacuum then stored in a moisture-free environment.

For each test, the catalyst tested was mixed with 50 g of this paste, then the catalytic potential was evaluated in the same way as before.

Various catalysts according to the invention were tested.

By way of comparison, as above, the following was also tested:

a tin-based catalyst: dibutyltin dilaurate.

The results are given in table II below:

TABLE II

| Reference | Product | mol/Sn | wt % | SOT stick min | Tacky feel at 48 h | Shore A hardness over 6 mm | | | | | | | | | | 7 d RT + 7 d 100° C. | |
|---|---|---|---|---|---|---|---|---|---|---|---|---|---|---|---|---|
| | | | | | | 2 d | | 3 d | | 4 d | | 7 d | | 14 d | | |
| | | | | | | > | < | > | < | > | < | > | < | > | < | > | < |
| Comparative | DBTDL | 1 | 1.1 | 60 | no | 10 | 7 | 16 | 12 | 20 | 16 | 26 | 22 | 32 | 29 | 33 | 29 |

TABLE II-continued

| Reference | Product | mol/Sn | wt % | SOT stick min | Tacky feel at 48 h | Shore A hardness over 6 mm | | | | | | | | | | | |
|---|---|---|---|---|---|---|---|---|---|---|---|---|---|---|---|---|---|
| | | | | | | 2 d > | 2 d < | 3 d > | 3 d < | 4 d > | 4 d < | 7 d > | 7 d < | 14 d > | 14 d < | 7 d RT + 7 d 100° C. > | 7 d RT + 7 d 100° C. < |
| 5 | 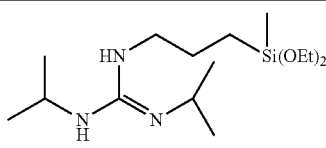 | 3 | 1.5 | 4 | no | 15 | 3 | 22 | 10 | 26 | 15 | 28 | 20 | 28 | 22 | 18 | 13 |
| 10 | 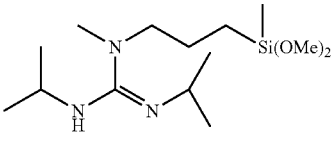 | 3 | 1.3 | 7 | no | 18 | 6 | 22 | 13 | 24 | 16 | 25 | 20 | 25 | 22 | 24 | 21 |
| 13 | 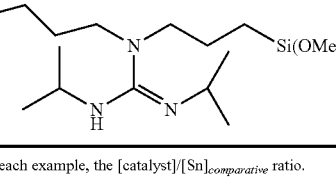 | 3 | 1.5 | 6 | no | 22 | 6 | 28 | 13 | 28 | 15 | 29 | 23 | 29 | 25 | 29 | 25 |

(1) Indicates, for each example, the [catalyst]/[Sn]$_{comparative}$ ratio.

The tin-based catalyst gives a good hardness but only at 7 days with this much less reactive system. Furthermore, the skin-over time is prohibitive. With the catalysts according to the invention, the skin-over times are short and the hardness kinetics much faster. An elastomer that releases virtually only ethanol is therefore made possible with the catalysts according to the invention.

11. Two-Component Compositions

The comparison of the activity of the catalysts according to the invention with respect to the standard catalyst (dimethyltin bisneodecanoate—UL28) was carried out on a simplified system: mixed with 25 g of an α,ω-dihydroxylated oil with a viscosity of 14 000 centipoise containing 0.065% of OH are 1.06 g of "advanced" (=partially hydrolyzed) ethyl silicate, then the same molar amount of catalyst (0.7 mmol) listed as wt % in table III. The working time or gel time was measured, followed by the hardnesses of a 6 mm thick part. In the case of the silylated guanidines, the gel time of which is very short, it is possible to first add a molar equivalent or less of a carboxylic acid in order to form, in situ, a less reactive guanidinium salt.

TABLE III

| Reference | Product | wt % | Gel time min | Shore A hardness 6 mm | | | | | |
|---|---|---|---|---|---|---|---|---|---|
| | | | | 24 h > | 24 h < | 6 days > | 6 days < | n days > | n days < |
| Comparative | UL28 | 1.4 | 15 | 24 | 19 | 25 | 25 | 23 | 23 (21 d) |
| 5 | 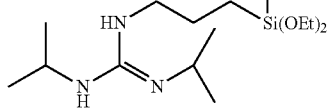 | 0.8 | 0.5 | 22 | 6 | 24 | 23 | 23 | 22 (28 d) |
| | guanidinium salt of compound 5 (n-octanoate derivative of compound 5) | 1.2 | 18 | 17 | 15 | 25 | 25 | 26 | 26 (28 d) |
| 10 | 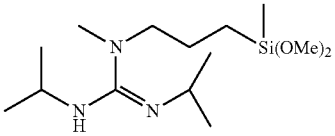 | 0.7 | 2.5 | 22 | 6 | 24 | 24 | 22 | 22 (21 d) |
| | guanidinium salt of compound 10 (n-octanoate derivative of compound 10) | 1.1 | 80 | 10 | 11 | 22 | 23 | 22 | 25 (13 d) |

At 6 days, all the catalyst systems are equivalent. The formation of guanidinium salts makes it possible to adjust the high reactivity of the catalysts according to the invention.

The invention claimed is:

1. A compound corresponding to the general formula (I):

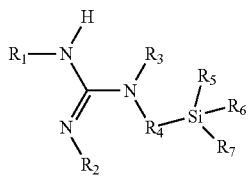
(I)

wherein:
- $R_1$ and $R_2$, which are identical or different, represent, independently of one another, a linear or branched monovalent alkyl group, a cycloalkyl group, a (cycloalkyl)alkyl group, the ring being substituted or unsubstituted and optionally comprising at least one heteroatom, an arylalkyl, fluoroalkyl, substituted or unsubstituted aryl or $R_{11}R_{12}R_{13}Si$ group, where $R_{11}$, $R_{12}$, and $R_{13}$ are linear or branched monovalent alkyl groups;
- $R_3$ represents a hydrogen atom, a linear or branched monovalent alkyl group, a cycloalkyl group, an alkyl group substituted by a ring that is substituted or unsubstituted and that optionally comprises at least one heteroatom, an arylalkyl, fluoroalkyl, alkylamine, alkylguanidine or substituted or unsubstituted aryl group or an alkylalkoxysilane;
- $R_4$ represents a linear or branched alkyl chain containing 1 to 50 atoms some of them optionally being heteroatoms chosen from O, S and N;
- $R_5$, $R_6$ and $R_7$, which are identical or different, represent, independently of one another, a linear or branched alkyl group, an aromatic group, an alkoxy group or a trialkylsilyloxy group of formula (I') below:

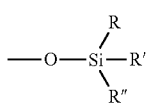
(I')

R, R' and R", which are identical or different, represent, independently of one another, a linear or branched $C_1$-$C_{12}$ alkyl group or an aromatic group; and on condition that:
- if $R_3$ is a hydrogen atom, then $R_1$ and $R_2$ are not, either of them, a linear monovalent hydrocarbon-based group;
- if $R_1$ and $R_2$ are each a cyclohexyl group, $R_4$ a linear propylene group and $R_5=R_6=R_7=OEt$, then $R_3$ is not a hydrogen atom; and
- if $R_1$ and $R_2$ are each a cyclohexyl group, $R_4$ a linear propylene group and $R_5=R_6=R_7=OEt$, then $R_3$ is not the group

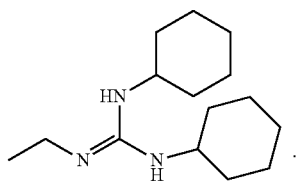 [SMILES: CCN=C(NC1CCCCC1)NC1CCCCC1]

2. The compound as claimed in claim 1, wherein $R_1$ and $R_2$ are each an isopropyl or a cyclohexyl group.

3. The compound as claimed in claim 1, wherein $R_3$ is a hydrogen atom, a methyl group, an ethyl group, a propyl group, a butyl group, or a propyltrialkoxysilane group.

4. The compound as claimed in claim 1, that is chosen from the compounds (1) to (54) below:

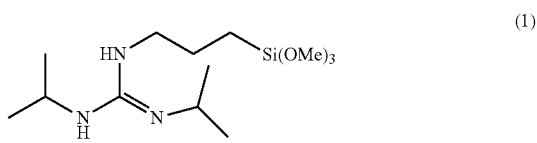
(1)

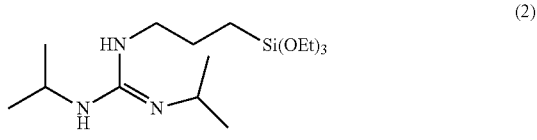
(2)

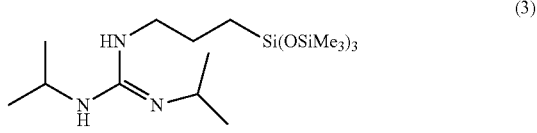
(3)

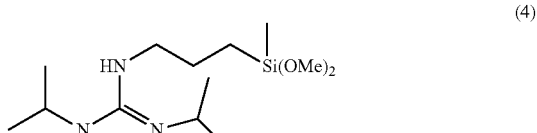
(4)

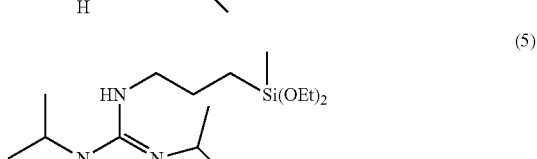
(5)

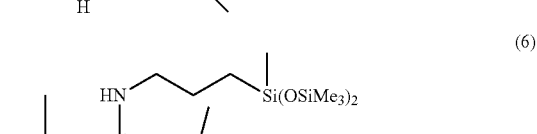
(6)

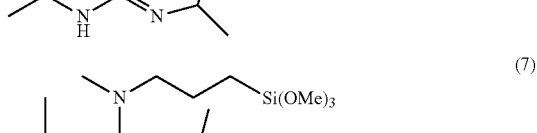
(7)

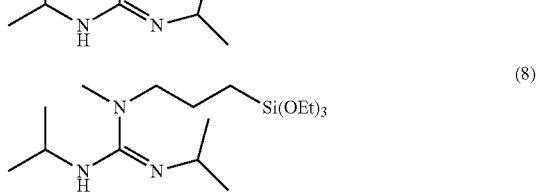
(8)

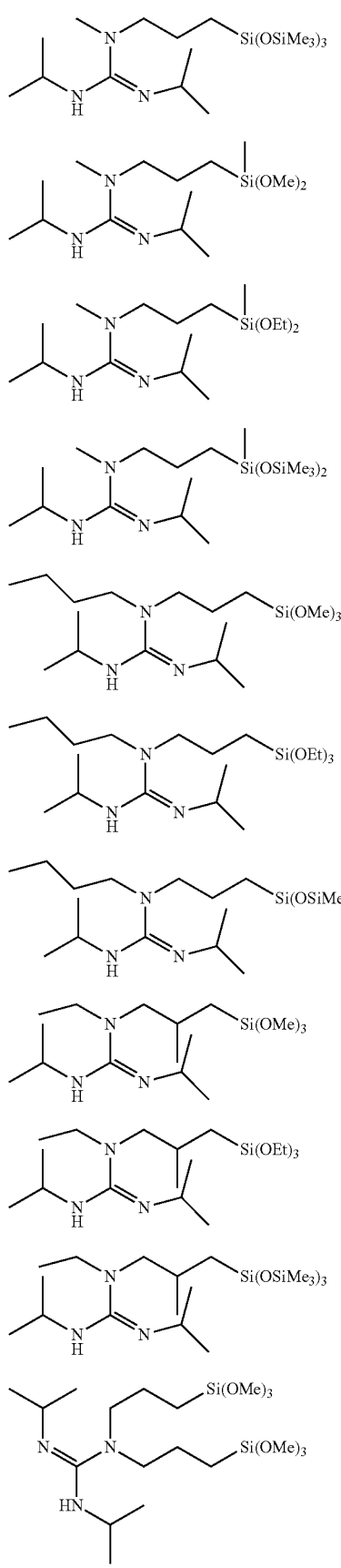
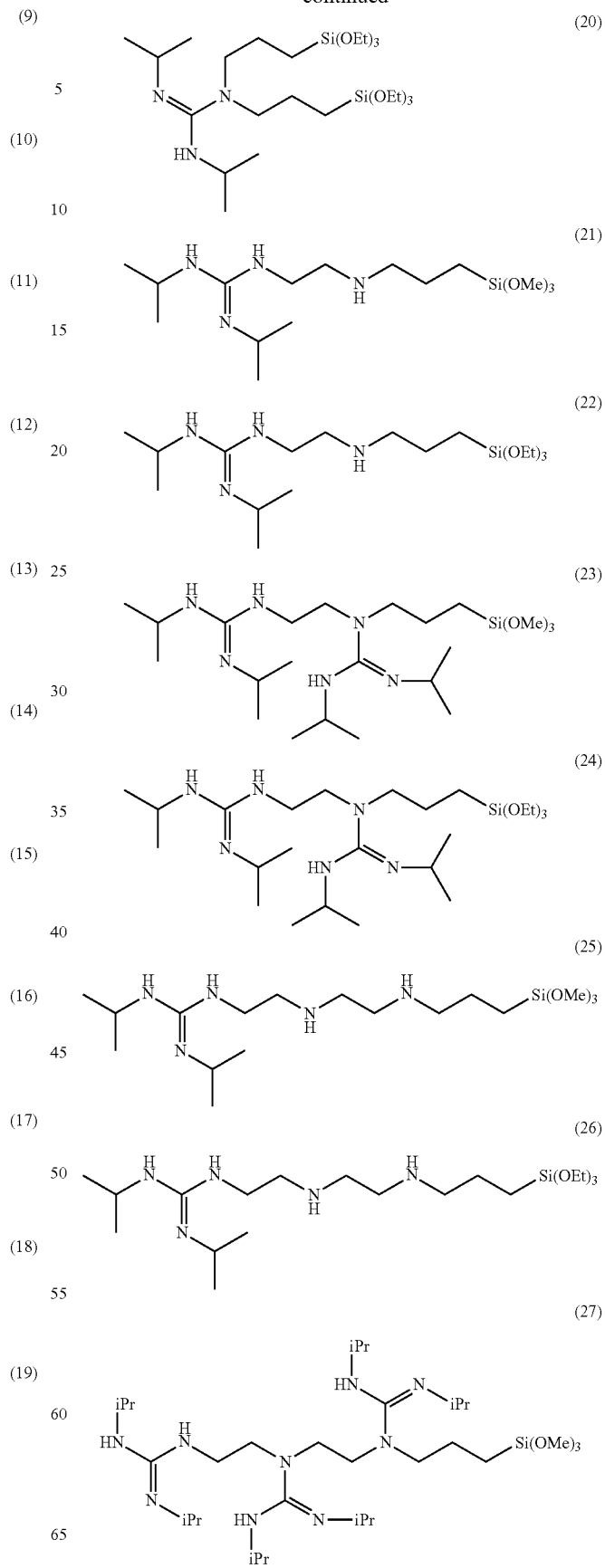

(28)
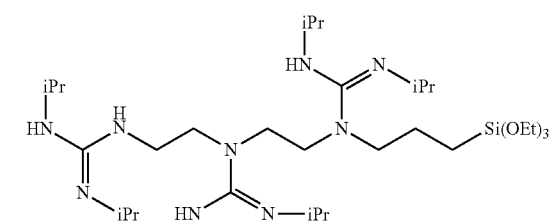
(29)
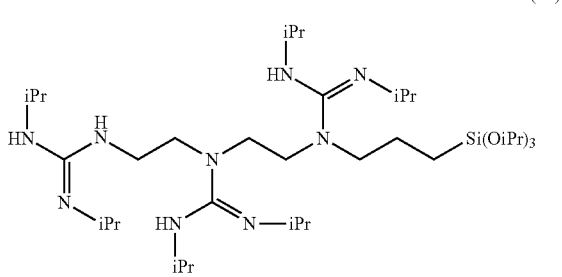
(30)
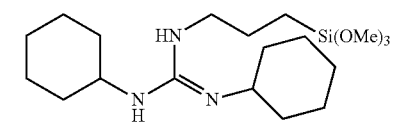
(31)
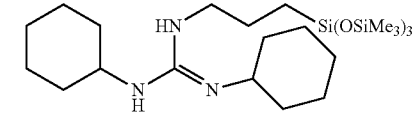
(32)
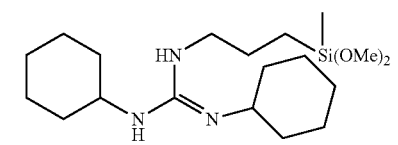
(55)
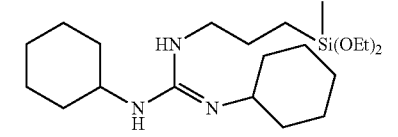
(33)
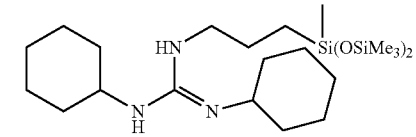
(34)
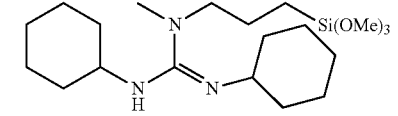
(35)
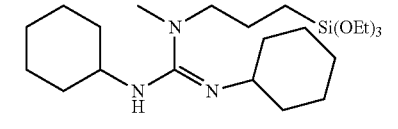
(36)
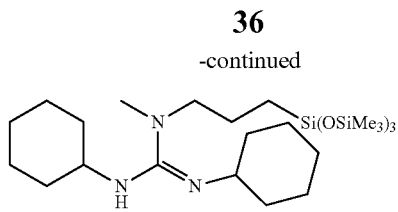
(37)
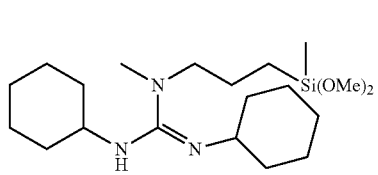
(38)
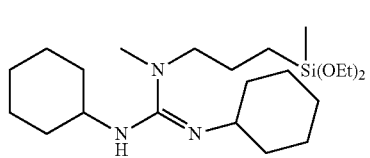
(39)
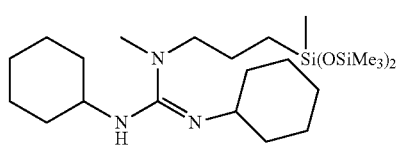
(40)
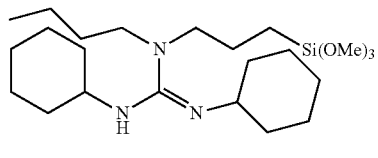
(41)
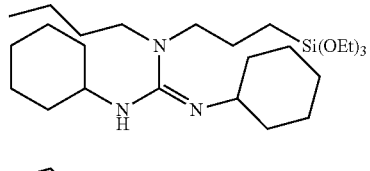
(42)
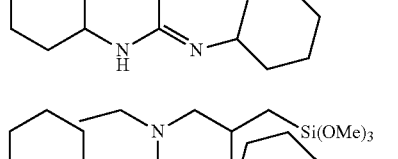
(43)
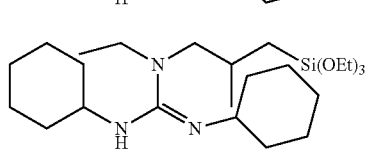
(44)
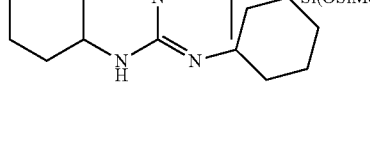
(45)

-continued

(46)
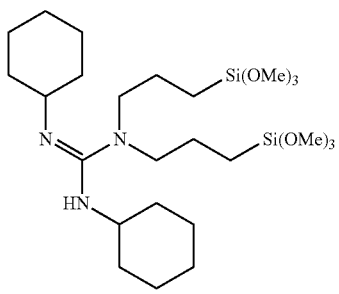

(47)
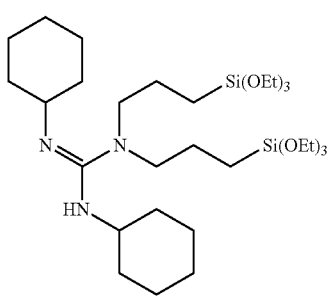

(48)
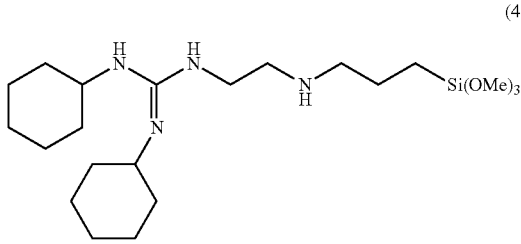

(49)
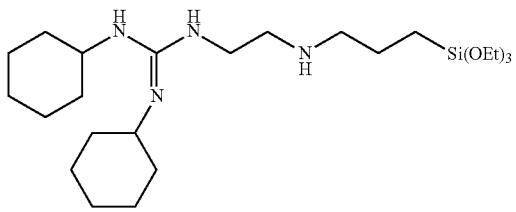

(50)
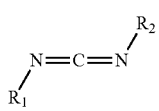

(51)
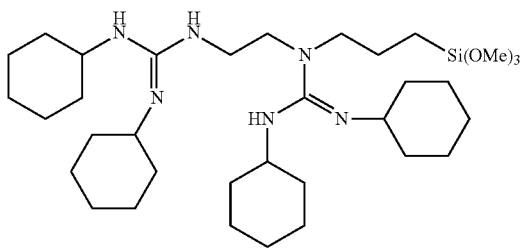

-continued

(52)
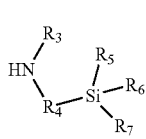

(53)

(54)

5. A process for preparing a compound of formula (I) as claimed in claim 1, comprising reacting a carbodiimide of formula (II):

$$\underset{R_1}{N}=C=\underset{}{N}{R_2} \quad (II)$$

with a primary or secondary amine of formula (III):

$$HN\underset{R_4}{\overset{R_3}{\diagdown}}\underset{}{Si}\underset{R_7}{\overset{R_5}{\diagup}}{R_6} \quad (III)$$

where $R_1$, $R_2$, $R_3$, $R_4$, $R_5$, $R_6$ and $R_7$ are as defined above.

6. The process as claimed in claim 5, wherein the reaction of the carbodiimide of formula (II) with the amine of formula (III) is carried out without solvent.

7. A guanidinium salt (IV) prepared by reacting a compound as claimed in claim 1 with an acid.

8. An organopolysiloxane composition, comprising a silicone base B capable of curing via polycondensation reaction into a silicone elastomer and a catalytically effective amount of at least one polycondensation catalyst which is either a guanidinium salt (IV) as defined as claimed in claim 7 or a guanidine of formula (I) below:

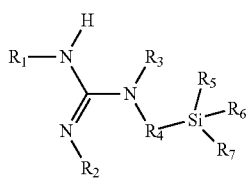

(I)

wherein:
- $R_1$ and $R_2$, which are identical or different, represent, independently of one another, a linear or branched monovalent alkyl group, a cycloalkyl group, a (cycloalkyl)alkyl group, the ring being substituted or unsubstituted and optionally comprising at least one heteroatom, an arylalkyl, fluoroalkyl, substituted or unsubstituted aryl or $R_{11}R_{12}R_{13}Si$ group, where $R_{11}$, $R_{12}$, and $R_{13}$ are linear or branched monovalent alkyl groups;
- $R_3$ represents a hydrogen atom, a linear or branched monovalent alkyl group, a cycloalkyl group, an alkyl group substituted by a ring that is substituted or unsubstituted and that optionally comprises at least one heteroatom, an arylalkyl, fluoroalkyl, alkylamine, alkylguanidine or substituted or unsubstituted aryl group or an alkylalkoxysilane;
- $R_4$ represents a linear or branched alkyl chain containing 1 to 50 atoms, some of them optionally being heteroatoms chosen from O, S and N;
- $R_5$, $R_6$ and $R_7$, which are identical or different, represent, independently of one another, a linear or branched alkyl group, an aromatic group, an alkoxy group or a trialkylsilyloxy group of formula (I') below:

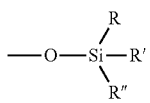

(I')

R, R' and R", which are identical or different, represent, independently of one another, a linear or branched $C_1$-$C_{12}$ alkyl group or an aromatic group;

on condition that if $R_3$ is a hydrogen atom, then $R_1$ and $R_2$ are not, either of them, a linear monovalent hydrocarbon-based group.

9. A composition as comprising a silicon base B, and a polycondensation catalyst comprising a compound chosen from the compounds (1) to (54) as defined in claim 4, wherein the silicone base B comprises:
- at least one polyorganosiloxane oil C capable of crosslinking via polycondensation into an elastomer;
- optionally at least one crosslinking agent D;
- optionally at least one adhesion promoter E; and
- optionally at least one siliceous, organic and/or non-siliceous mineral filler F.

10. The composition as claimed in claim 8, wherein the amount of compound of formula (I) is from 0.1% to 10% by weight of the total weight of said composition.

11. The composition as claimed in claim 8, wherein the silicone base B comprises:
- at least one polyorganosiloxane oil C capable of crosslinking via polycondensation into an elastomer;
- optionally at least one crosslinking agent D;
- optionally at least one adhesion promoter E; and
- optionally at least one siliceous, organic and/or non-siliceous mineral filler F.

12. An elastomer obtained by crosslinking and curing the composition as claimed in claim 8.

13. A catalyst for the polycondensation reaction of organopolysiloxanes comprising a guanidinium salt (IV) as defined as claimed in claim 7.

14. A catalyst for the polycondensation reaction of organopolysiloxanes comprising compound of formula (I):

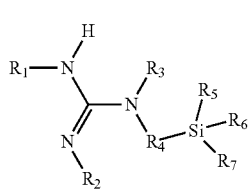

(I)

in which:
- $R_1$ and $R_2$, which are identical or different, represent, independently of one another, a linear or branched monovalent alkyl group, a cycloalkyl group, a (cycloalkyl)alkyl group, the ring being substituted or unsubstituted and optionally comprising at least one heteroatom, an arylalkyl, fluoroalkyl, substituted or unsubstituted aryl or $R_{11}R_{12}R_{13}Si$ group, where $R_{11}$, $R_{12}$, and $R_{13}$ are linear or branched monovalent alkyl groups;
- $R_3$ represents a hydrogen atom, a linear or branched monovalent alkyl group, a cycloalkyl group, an alkyl group substituted by a ring that is substituted or unsubstituted and that optionally comprises at least one heteroatom, an arylalkyl, fluoroalkyl, alkylamine, alkylguanidine or substituted or unsubstituted aryl group or an alkylalkoxysilane;
- $R_4$ represents a linear or branched alkyl chain containing 1 to 50 atoms, some of them optionally being heteroatoms chosen from O, S and N;
- $R_5$, $R_6$ and $R_7$, which are identical or different, represent, independently of one another, a linear or branched alkyl group, an aromatic group, an alkoxy group or a trialkylsilyloxy group of formula (I') below:

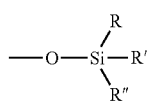

(I')

R, R' and R", which are identical or different, represent, independently of one another, a linear or branched $C_1$-$C_{12}$ alkyl group or an aromatic group; and on condition that: if $R_3$ is a hydrogen atom, then $R_1$ and $R_2$ are not, either of them, a linear monovalent hydrocarbon-based group;

if $R_1$ and $R_2$ are each a cyclohexyl group, $R_4$ a linear propylene group and $R_5=R_6=R_7=OEt$, then $R_3$ is not a hydrogen atom; and if $R_1$ and $R_2$ are each a cyclohexyl group, $R_4$ a linear propylene group and $R_5=R_6=R_7=$OEt, then $R_3$ is no the group

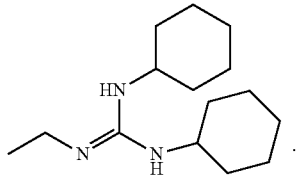 [SMILES: CCN=C(NC1CCCCC1)NC1CCCCC1]

15. The compound as claimed in claim 1, wherein $R_4$ represents a linear or branched alkyl chain containing 1 to 20 atoms, some of them optionally being heteroatoms chosen from O, S and N.

16. The composition as claimed in claim 8, wherein $R_4$ represents a linear or branched alkyl chain containing 1 to 20 atoms, some of them optionally being heteroatoms chosen from O, S and N.

17. The composition as claimed in claim 13, wherein $R_4$ represents a linear or branched alkyl chain containing 1 to 20 atoms, some of them optionally being heteroatoms chosen from O, S and N.

* * * * *